(12) United States Patent
Chawla et al.

(10) Patent No.: US 8,114,678 B2
(45) Date of Patent: Feb. 14, 2012

(54) MULTI-DIMENSIONAL HIGH PERFORMANCE LIQUID CHROMATOGRAPHIC SEPARATION TECHNIQUE (STAR7) FOR QUANTITATIVE DETERMINATIONS OF 7 FRACTIONS IN HEAVY PETROLEUM STREAMS BOILING ABOVE 550 DEGREES F

(75) Inventors: Birbal Chawla, Mickleton, NJ (US); Larry A. Green, Mickleton, NJ (US)

(73) Assignee: ExxonMobil Research & Engineering Company, Annandale, NJ (US)

( * ) Notice: Subject to any disclaimer, the term of this patent is extended or adjusted under 35 U.S.C. 154(b) by 22 days.

(21) Appl. No.: 12/658,566

(22) Filed: Feb. 5, 2010

(65) Prior Publication Data
US 2010/0218585 A1    Sep. 2, 2010

Related U.S. Application Data

(60) Provisional application No. 61/208,457, filed on Feb. 24, 2009.

(51) Int. Cl.
*G01N 30/02*    (2006.01)
*B01D 15/00*    (2006.01)

(52) U.S. Cl. ......... 436/161; 436/139; 422/68.1; 422/70; 210/660

(58) Field of Classification Search .................. 436/161, 436/139; 422/68.1, 70; 210/660
See application file for complete search history.

(56) References Cited

U.S. PATENT DOCUMENTS

| | | | |
|---|---|---|---|
| 4,430,205 | A | 2/1984 | Felsky |
| 4,826,603 | A | 5/1989 | Hayes, Jr. et al. |
| 4,851,355 | A | 7/1989 | Hayes, Jr. et al. |
| 6,339,182 | B1 | 1/2002 | Munson et al. |
| 6,399,803 | B1 | 6/2002 | Corley et al. |
| 6,577,392 | B1 | 6/2003 | Nielson et al. |
| 6,849,774 | B2 | 2/2005 | Boudreau et al. |

OTHER PUBLICATIONS

Padlo et al., Fuel Processing Technology, 49:247-258, 1996.*
P.L. Grizzle, et al. Liquid Chromatographic Separation of Aromatic Hydrocarbons with Chemically Bonded (2,4 Dinitroanilinopropyl) silica. Analytical Chemistry, Jun. 1982; 54(7): 1071-1078.
K.J. Welch, et al. Physico-Chemical properties of Electron-Acceptor Stationary Phases in Liquid Chromatography. Journal of Chromatography A, Feb. 7, 1992; 591(1-2): 75-88.

* cited by examiner

*Primary Examiner* — Jill Warden
*Assistant Examiner* — Monique Cole
(74) *Attorney, Agent, or Firm* — Ronald D. Hantman; Glenn T. Barrett

(57) ABSTRACT

The present invention provides quantitation of seven classes of compounds (saturates, 1-4+ ring aromatics, sulfides, and polars) present in petroleum streams boiling from 550-1050° F. Operating the present invention in the preparative mode will allow us to load and collect multi-milligram amounts of material. In the present invention, all seven fractions are produced in a single run, whereas the most commonly used preparative liquid chromatographic separations requires two or more large scale separations to generate similar fractions. The present invention uses 100 times less solvent. The present invention protocol provides a quicker and cheaper alternative to most commonly used preparative liquid chromatographic separations and is flexible enough to target many refining and chemicals problems.

9 Claims, 11 Drawing Sheets

STAR7 System Configuration

Chromatographic Separation of Six Classes of Model Compounds

STAR7 Separation Chromatogram of a Petroleum Distillate

Comparisons between START7 and Preparative HPLC Results

Comparisons between START7 and Preparative HPLC Results

Two Preparative HPLC Separation Steps

US 8,114,678 B2

MULTI-DIMENSIONAL HIGH PERFORMANCE LIQUID CHROMATOGRAPHIC SEPARATION TECHNIQUE (STAR7) FOR QUANTITATIVE DETERMINATIONS OF 7 FRACTIONS IN HEAVY PETROLEUM STREAMS BOILING ABOVE 550 DEGREES F

This Application claims the benefit of U.S. Provisional Application 61/208,457 filed Feb. 24, 2009.

BACKGROUND OF THE INVENTION

The present invention relates to a method and system for analyzing hydrocarbon containing oils. In particular, the present invention relates to the chromatographic analysis of hydrocarbon containing oils to provide quantification of seven classes of compounds (saturates, 1-4$^+$ ring aromatics, sulfides, and is polars).

Compositional analysis of heavy petroleum streams is essential in order to improve efficiency of refinery operations. However, these streams are too complex to be analyzed as such, for detailed compositional information, even with the most modern analytical techniques/instruments. It is, therefore, essential to fractionate them into sub-groups of different classes of compounds so that the detail/extensive molecular compositional analyses can be performed using characterizing tools, e.g. high resolution mass spectroscopy. Preparative liquid chromatography (LC) has been used very extensively to fractionate heavy streams in terms of mainly three classes of compounds, namely 'saturates' (consist of n-paraffins, iso-paraffins, and naphthenes), 'aromatics' (consists of aromatic-hydrocarbons, aromatic-thiophenes, and some sulfides), and 'polars' (consists of heteroatom containing complex organic compounds). Additionally, 'aromatics' are further fractionated, using preparative liquid chromatography, mostly into four classes of aromatic compounds based upon number of aromatic rings such as one-, two-, three-, and four+-rings. Although these preparative liquid chromatographic approaches provide relatively pure fractions and the weight percent data, the LC separations are very laborious and time consuming and hence costly. Additionally, these separations are not very environmental friendly because they use large volume of organic solvents which must be evaporated in order to get pure fractions. On many occasions, particularly for R&D projects only weight percent data for various fractions are needed.

The present invention provides quantitation of seven classes of compounds (saturates, 1-4+ ring aromatics, sulfides, and polars) present in petroleum streams boiling from 550-1050° F. Operating the present invention in the preparative mode will allow us to load and collect multi-milligram amounts of material. In the present invention, all seven fractions are produced in a single run, whereas the most commonly used preparative liquid chromatographic separations requires two or more large scale separations to generate similar fractions. The present invention uses 100 times less solvent. The present invention protocol provides a quicker and cheaper alternative to most commonly used preparative liquid chromatographic separations and is flexible enough to target many refining and chemicals problems.

SUMMARY OF THE PRESENT INVENTION

The present invention is an automated analytical high performance liquid chromatographic (HPLC) method for rapid quantitative determination of seven classes of compounds present in heavy petroleum streams boiling between 550° F. and 1050° F. The vacuum gas oil (VGO) samples are covered in this boiling range. The seven classes of compounds are: 'Saturates', 'Aromatic-Ring-Classes 1-4 (4 fractions)', 'Sulfides', and 'Polars'. The HPLC method of the present invention is called START (Synthesis TARget of 7 classes of compounds). Results from this type of analysis relates to the compositional analysis of both refinery and research samples. Synthesis refers to a data reconciliation procedure in which a detailed model-of-composition is adjusted to match analytical test results referred to as targets. Models-of-composition and a data reconciliation procedure are described in US 2007/0114377A1, Micro-Hydrocarbon Analysis. STAR7 provides seven analytical test results that are used in the reconciliation process. STAR7 may be employed as part of the analytical protocol used in developing a model of composition for a hydrocarbon sample. In addition, STAR7 can provide targets to which a reference model-of-composition is reconciled in estimating a model-of-composition for a sample under test.

The data obtained in separations can be used to reconcile other measurements including other chromatographic separations methods and MS or GC/MS data. The molecular composition information obtained by using this method with further analysis by GC and MS methods can be used to develop and apply refinery process models for process optimization, monitoring and troubleshooting, feedstock and catalyst selection, and serve as a reference of typical stream compositions (see R. J. Quann and S. B. Jaffe (Ind. Eng. Chem. Res., 1992, 31, 2483-2497 and Quann, R. J. and Jaffe, S. B. Chemical Engineering Science v51 no 10 pt A May 1996, p 1615-1635, 1996).

The present invention includes the features discussed below.

The development of the system includes two features. First, the use of both a silver ion loaded strong cation exchange (Ag$^+$/SCX) column for 'sulfides' separation and a new more retentive charge transfer column for superior separation of aromatic-ring classes and 'polars' compounds. Second, the optimization of a newly marketed evaporative light scattering detector (ELSD) to extend its use for the first time for quantitative determination to the lower boiling materials of above 550° F.

A new calibration approach for the evaporative light scattering detector (ELSD) for accurate determination of seven classes of compounds, namely 'Saturates', 'Aromatic-Ring-Classes 1-4+ (4 fractions)', 'Sulfides', and 'Polars'.

STAR7 analysis of a sample takes about 150 minutes to complete and a set of twenty-five samples could be analyzed unattended. Sample preparation takes approximately 60 minutes per ten samples. In a typical analysis, 40 micro-liters of a 10-mg/ml sample-solution in cyclohexane are injected into the STAR7 system.

Comparison of the results from this new analytical method (STAR7) with those of the very time consuming preparative liquid chromatographic separations shows very good agreement for all of the 7 classes of compounds (saturates, 1-4+ ring aromatics, sulfides, and polars). The STAR7 results can be used along with other analyses such as density, GC-simulated distillation, % S and % N as targets for "synthesis" of full compositional details of the heavy petroleum stream. Because the amounts of the classes of compounds obtained using STAR7 are composition) information, the accuracy of a synthesized composition using these amounts as targets is higher.

The analytical STAR7 system can also be modified so that much heavier samples (de-asphalted oils of vacuum resides) can be analyzed.

The analytical STAR7 system can be modified by adding a fraction collector to run in the preparative mode to collect fraction for further analyses by NMR. GC, and GC-TOF-MS. These analyses would provide detail compositional information of various classes of compounds present in the heavy petroleum streams.

A modification of the STAR7 allows an accurate determination of total saturates content and 1-4 ring aromatics distribution for high quality Group II/III lube basestocks. The STAR7 data has been used to quantify the aromatics of dozens of Group II and III basestocks to expand the database from which to build improved UV-aromatics correlations.

Major differences between the present invention and the prior art of high performance liquid chromatographic separation method (HPLC) are discussed below.

STAR7 is suitable for 550+F samples instead of 650+F (HPLC2: U.S. Pat. Nos. 4,988,446 & 5,076,909) and, hence, eliminates distillation requirement for samples having a 550-650F fraction.

STAR7 uses both a silver ion loaded strong cation exchange silica gel based ($Ag^+/SCX^-$-SG) column for 'sulfides' separation and a new more retentive charge transfer silica gel based column (DNAP-SG) for superior separation of aromatic-ring classes and 'polars' compounds. HPLC2 uses much less retentive columns (DNAP and PAC) which do not provide nearly as good separations as STAR7. [See Example 3]

STAR7 uses a newly marketed evaporative light scattering detector (ELSD) to extend its use for the first time for quantitative determination to the lower boiling materials as compared to that of HPLC2.

STAR7 provides baseline separated narrow peaks for 7 classes of compounds, and hence more precise quantitation.

STAR7 provides accurate quantitative data similar to that of very time consuming preparative liquid chromatographic separations.

STAR7 provides quantitation of an additional class of compounds, 'sulfides'.

The separating columns in STAR7 are back-flushed for 'polars' and 'sulfides' recoveries which result in sharp peaks and hence more precise quantitation. Additionally, the columns are cleaned more thoroughly in this process and are ready to be used for next separation.

Relatively narrow peaks and hence easier to use STAR7 separation for further analysis with a GC, MS, or GC/MS.

Very small amount of sample, as low as 2 mg, can be analyzed by STAR7. Also, several STAR7 analyses can be performed (if needed) from a single solution vial as compared to only one injection per vial in HPLC2. Sample solution preparation in HPLC2 requires about 150 mg of the material.

STAR7 is more robust because it is based on a newer instrumental technology as compared to about 20 years old instrumentation for the HPLC2 approach.

The analytical STAR7 can be modified to run in the preparative mode to collect fractions for further analyses by NMR, GC, and GC-TOF-MS etc.

The steps of the method for the chromatographic analysis of hydrocarbon oil include:

Step 1: passing a mixture of the hydrocarbon oil and a first solvent sequentially through a 2,4-dinitro-anilinopropyl-silica gel (DNAP) and a silver ion strong cation ion exchange column ($Ag^+/SCX^-$) to elute pure 'saturate' fraction of said oil and sending it to an evaporative light scattering detector (ELSD), Step 2: passing a solvent through $Ag^+/SCX^-$) to elute a fraction of the hydrocarbon oil, repeating steps 1 and 2 only with solvents chosen to elute different fractions of the hydrocarbon oil, and back-flushing of the hydrocarbon oil, and back-flushing DNAP and $Ag^+/SCX^-$ to elute different fractions, sending the eluting fractions to an evaporative light scattering detector (ELSD).

DETAILED DESCRIPTION OF THE PREFERRED EMBODIMENT

Figure 1:
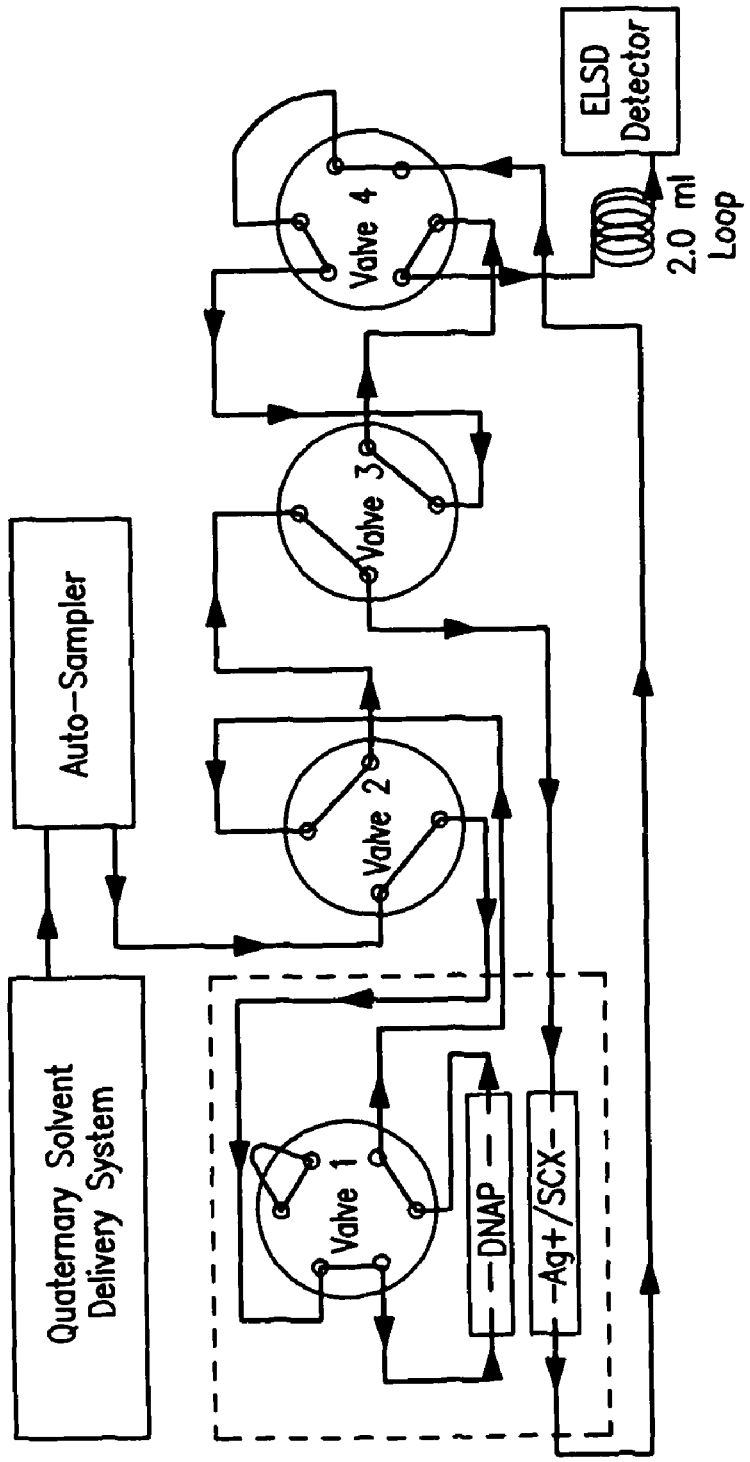
FIG. 1 shows a schematic diagram of the switching valves arrangement for the system of the present invention set for the elution of saturates.

As shown in FIG. 1, the STAR7 system was assembled using an Agilent 1100 quaternary solvent delivery pump equipped with a degasser, thermostated column compartment, 1100 Agilent photo-diode array detector (DAD—used only during method development and shown in STAR7 configuration), and four switching valves. The solvent delivery unit can be programmed to deliver one of the four different solvents or their mixture in a selected ratio for the specified duration at a desired rate of up to 10 ml/min.

An evaporative light scattering detector (ELSD), model PL-ELS 1000, was purchased from Polymer Laboratories Inc., Amherst, Mass.

The operation of the HPLC system is controlled by the Agilent ChemStation software system.

The more retentive charge transfer column for a better separation of aromatic ring classes (ARC) of compounds and a silver-ion-loaded strong cation exchange ($Ag^+/SCX^-$) for 'sulfides' separation were used. The two stainless steel analytical columns used for the STAR-7 separations are:

A stainless steel column (dimensions: 250 mm×4.6 mm) packed with 2,4-dinitro-anilinopropyl-silica gel (DNAP-SG) was purchased from the ES Industries Inc., Berlin, N.J.

A stainless steel column packed with silver-ion loaded strong cation ion-exchange-silica gel ($Ag^+/SCX^-$-SG, dimensions: 250 mm×4.6 mm) was purchased from Phenomenex.

Phenomenex prepared this column using LUNA$^R$ base silica having ultra-pure particles with the improved surface smoothness and particle sphericity. The consistent pore structure and extremely narrow pore size distribution provided by the LUNA$^R$ packing enhances column mechanical strength and hence highly reproducible separations for a relatively long time.

STAR7 Operational Procedure

The instrument method, which controls all the switching valves at the specified timing intervals, was created using the Agilent ChemStation. The instrument method also controls operation of the quaternary solvent system and rest of the separation system in such a way that both the columns were regenerated at the end of the run.

TABLE 1

Quaternary Pump Solvent Programming

| Initial Solvent: | Hexane | Initial Flow: | | 2.0 ml/min | |
|---|---|---|---|---|---|
| Run Stop Time: | 80 min. | Post Time: (System Regeneration) | | 60 min | |

| Elution Step | Time (min) | Hexane % | Methylene Chloride % | Methanol % | Toluene % | Flow Ml/min |
|---|---|---|---|---|---|---|
| Eluting Saturates & | 0.01 | 100 | 0 | 0 | 0 | 1.50 |
| Moving ARC-1 to Ag+/SCX− | 7.00 | 100 | 0 | 0 | 0 | 1.50 |
| Eluting ARC-1 | 8.00 | 0 | 98 | 0 | 2 | 1.50 |
|  | 9.00 | 0 | 100 | 0 | 0 | 1.50 |
| Moving ARC-2 to Ag+/SCX− | 11.00 | 92 | 8 | 0 | 0 | 1.50 |
|  | 16.00 | 92 | 8 | 0 | 0 | 1.50 |
| Eluting ARC-2 | 16.05 | 0 | 95 | 0 | 5 | 1.50 |
|  | 19.00 | 0 | 100 | 0 | 0 | 1.50 |
|  | 20.00 | 0 | 100 | 0 | 0 | 1.50 |
| Moving ARC-3 to Ag+/SCX− | 22.00 | 83 | 17 | 0 | 0 | 1.50 |
|  | 26.50 | 83 | 17 | 0 | 0 | 1.50 |
| Eluting ARC-3 | 26.55 | 0 | 90 | 0 | 10 | 1.50 |
|  | 30.00 | 0 | 100 | 0 | 0 | 1.50 |
| Moving ARC-4+ to Ag+/SCX− | 32.00 | 50 | 50 | 0 | 0 | 1.50 |
|  | 39.00 | 50 | 50 | 0 | 0 | 1.50 |
| Eluting ARC-4+ | 40.00 | 0 | 49 | 1 | 50 | 1.50 |
|  | 45.00 | 0 | 50 | 0 | 50 | 1.50 |
| Back-flushing Sulfides and | 45.05 | 0 | 40 | 10 | 50 | 1.50 |
| Polars | 66.00 | 0 | 40 | 10 | 50 | 1.50 |
| System Cleaning & | 66.05 | 0 | 100 | 0 | 0 | 1.50 |
| Regeneration | 68.00 | 0 | 100 | 0 | 0 | 1.50 |
|  | 68.01 | 100 | 0 | 0 | 0 | 2.50 |
|  | 100.00 | 100 | 0 | 0 | 0 | 0.00 |

FIG. 1 shows an arrangement of switching valves for the first step of a separation where the saturates fraction is eluted and then detected/quantified. The separation steps for eluting and then detecting/quantifying the other six fractions are performed as per programmed.

Figure 2:
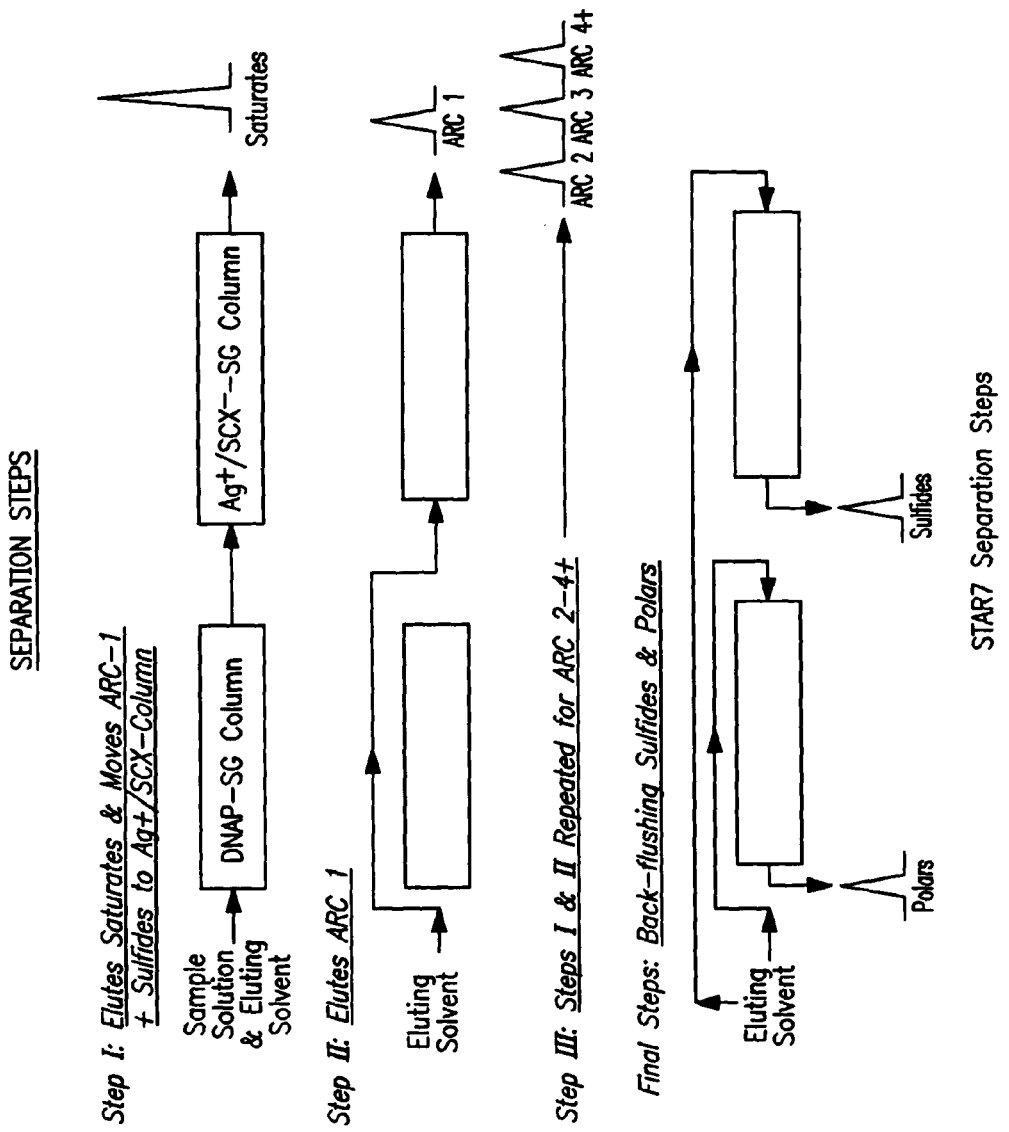
FIG. 2 shows a schematic diagram showing the separation steps of the present invention.

At the system start up, the solvent delivery system is programmed (Table 1) to run hexane at a flow-rate of 2.0 ml/min that changes to 1.5 ml/min at 0.01 minute run-time. As shown in FIGS. 1 & 2, the switching valves, during step 1 of the separation, are set in such a way that the mobile phase from the DNAP-SG column passes through the Ag+/SCX−-SG column and a 2.0 ml loop (to broaden the peak profile to improve detection) before going to the ELSD (detector).

This arrangement allows, in addition to the elution of "saturates", the transfer of "ARC-1 plus some Sulfides" to the Ag+/SCX−-SG column (see Step 1 in FIG. 2) only, whereas rest of the samples remains on DNAP-SG column. The "ARC-1" compounds are then eluted using more polar solvent mixture (see step II in FIG. 2), whereas the "ARC-1 sulfides" are retained by the Ag+/SCX−-SG column. Then steps I & II are repeated for "ARC-2" through "ARC-4+" classes of compounds. During the "saturates" and "ARC-1" through "ARC-4+" elution steps, the total "polars" and the total "sulfides" are retained by the DNAP-SG and Ag+/SCX−-SG columns, respectively. Finally, the "polars" and "sulfides" are eluted by back-flushing the two columns separately, as shown in final steps of FIG. 2, using a highly polar mixture of three solvents, namely methylene chloride, toluene, and methanol (see FIG. 2 and Tables 1 for more details). The solvents/solvent-combinations used for eluting different fractions are provided in Table 1.

Upon completion of a separation run, the system continues running for an additional 60 minutes to regenerate both columns before the next sample is injected.

Evaluation/Optimization of Analytical Columns

The two analytical HPLC columns, DNAP and Ag+/SCX− were initially evaluated by testing elution behavior of some selected model compounds with different mobile phases. During these evaluations, several neat solvents and their mixtures were used. At the very initial stages of column evaluation, we found out that the batch of the DNAP columns used was more retentive than the ones most commonly used. The high retentivity of the DNAP column provided greater flexibility in adjusting the mobile phase strength during separations of aromatic ring classes of compounds. Having significant prior experience with different batches of the DNAP, only a limited amount of HPLC work on the elution behavior of limited sets of aromatic model compounds was needed. Only two organic solvents, namely hexane & methylene chloride and their mixtures were used to learn the quality of separations of 1-, 2-, 3-, & 4+-ring aromatics (ARC 1-4+), and sulfides. The retention time (RT) data of model compounds and chromatographically separated fractions of a typical petroleum distillate (650-1000° F.) are provided in Table 2. The RT data clearly suggests that the DNAP column does not provide adequate separation of saturates (e.g., n-hexadecane) from 1-ring aromatics, even with a non-polar solvent, hexane. This can be seen by comparing the similar RT data (Table 2) of n-hexadecane with that of n-nonadecyl-benzene. However, the baseline separation between saturates and 1-ring-aromatics can be achieved by using the second column (Ag+/SCX−). The RT data (Tables 2 & 3) clearly establish that all the aromatic classes of compounds along with sulfides can be transported to the second column by adjusting the methylene chloride concentration in hexane.

TABLE 2

Retention Time Data in Minutes for DNAP Column
[Solvent Flow = 1.5 ml/min, Detector = DAD/ELSD]
[Mobile Phase (MP) = % Methylene Chloride in Hexane]

| Compound | Hexane | 5% | 10% | 20% | 30% | 50% | 75% | 100% |
|---|---|---|---|---|---|---|---|---|
| n-Hexadecane | 2.3 | 2.2 | 2.2 | 2.2 | 2.1 | 2.0 | 2.0 | |
| n-Nonadecyl-Benzene | 2.7 | 2.5 | 2.3 | 2.2 | 2.1 | 2.0 | 2.0 | |
| Naphthalene | 4.9 | 3.6 | 3.2 | 2.8 | 2.6 | 2.4 | 2.2 | |
| Benzothiophene | | 3.9 | 3.4 | 2.9 | 2.6 | 2.4 | 2.3 | |
| Phenanthrene | 15.2 | 8.4 | 11.5 | 4.0 | 3.2 | 2.6 | 2.4 | |
| Dibenzothiophene | | | | | 3.1 | 2.6 | 2.4 | 2.5 |
| 4,6-Me2-Dibenzothiophene | | | | | 3.1 | 2.6 | 2.3 | |
| Pyrene | Retained | | | 25.3 | 4.2 | 3.2 | 2.7 | |
| n-Dodecylsulfide | | | | | 2.2 | | | 2.1 |
| Phenyl hexadecyl sulfide | | | | | 2.4 | | | 2.0 |
| Distillate Sulfides | | | | | 2.4 | | | 2.1 |
| Distillate Total Aromatics | | | | | | | | 2-4 |
| Distillate ARC-1 | | 2.3-3.0 | | | | | | |
| Distillate ARC-2 | | 2.2-6.5 (broad) | | | | | | |
| Distillate ARC-3 | | | | 3-8 (broad) | | | | |
| Distillate ARC-4+ | | | | 5-15 (broad) | | | | |

[DAD = Diode Array Detector, ELSD = Evaporative Light Scattering Detector]

As shown by the RT data in Table 3, a baseline separation between saturates (n-hexadecane, RT=2.3 min) and 1-ring aromatics (n-nonadecyl-benzene, RT 5.8 min) can be achieved even with a relatively high polarity mobile phase (20% methylene chloride in hexane). It was interesting to observe that the higher ring aromatics were strongly retained.

A highly polar mobile phase (100% methylene chloride) was able to elute only about 85% of the total aromatics. In order to elute the total aromatics completely, 1% iso-propanol (IPA) in 99% methylene chloride was needed. However, most of the sulfides ~90%) were still retained. In order to elute sulfides completely, about 10% IPA in 90% methylene to chloride was required. The IPA solvent can be replaced by methanol.

TABLE 3

Retention Time Data in Minutes for $Ag^+/SCX^-$ Column
[Solvent Flow = 1.5 ml/min, Detector = DAD/ELSD]
[Mobile Phase (MP) = % Methylene Chloride (MC) in Hexane]

| Compound | 20% MC | 50% MC | 100% MC | 1% IPA + 99% MC | 2% IPA + 98% MC | 10% IPA + 90% MC |
|---|---|---|---|---|---|---|
| n-Hexadecane | 2.3 | 2.2 | 2.2 | | | |
| n-Nonadecyl-Benzene | 5.8 | 3.3 | 2.6 | | | |
| Naphthalene | 24.5 | 9.3 | 4.1 | | | |
| Benzothiophene | Retained | 11.3 | 4.5 | | | |
| Phenanthrene | | 26.9 | 6.9 | | | |
| Dibenzothiophene | | 28.3 | 8.4 | | | |
| Pyrene | | 34.1 (broad) | 9.7 (broad) | | | |
| 4,6-Me2-Dibenzothiophene | | 65 (broad) | 17.6 | | | |
| Total Dist. Aromatics | | | 2.8-25 (85% eluted) | 2-10 (99% eluted) | 2.5 | |
| Total Dist. Sulfides | | | Retained | Retained (90%) | 2.3 (90% eluted) | 2.5 |
| n-Dodecylsulfide | | | Retained | | | 2.3 |
| Phenyl hexadecyl sulfide | | | Retained | | | 2.3 |

Based upon the retention time data in Table 3, the benzothiophenes and dibenzothiophenes should follow the ring class separation behavior. For example, benzothiophene and dibenzothiophenes elute close to the 2-ring and 3-ring aromatics, respectively. However, the more retentive behavior of 4,6-dimethyl-dibenzothiophene is not understood at this time.

This column was also tested with hexane and toluene, and their mixtures to learn about the elution behaviors of saturates, aromatics, and sulfides of 550+F boiling point samples. We also found that the saturates are eluted completely with hexane solvent, whereas 100% toluene was able to elute aromatics almost completely and the sulfides were retained. All this combined RT information was necessary for the development of the START separation method.

Evaluation of Evaporative Light Scattering Detector (ELSD)

Evaporative light scattering detectors are the best known as relatively less complicated, inexpensive, very reliable, and easy to use mass detectors with HPLC systems. ELSDs were initially developed mostly for pharmaceutical applications and became available to the rest of the analytical community only about a couple of decades ago. In an ELSD, the HPLC mobile phase is removed by evaporation under a high flow of nitrogen after the effluent emerges out of the HPLC column, and then finally the solvent free solute particles of interest are detected by a light scattering technique. Under the most commonly used conditions (the solvent, evaporating temperature, and the nitrogen flow rate), most of the organic molecules boiling below 650° F. are lost during solvent evaporation and hence are not detected by the ELSD. However, we were able to optimize an ELSD to detect quantitatively the heavy petroleum streams boiling between 550-1050° F. (vacuum gas oil samples). A modified version of the ELSD-1000 from Polymer Lab. was used. By using a neutral density filter, the ELSD-1000 was tuned to filter off about 80% intensity of its light source, thus increasing its detection range.

Figure 3:
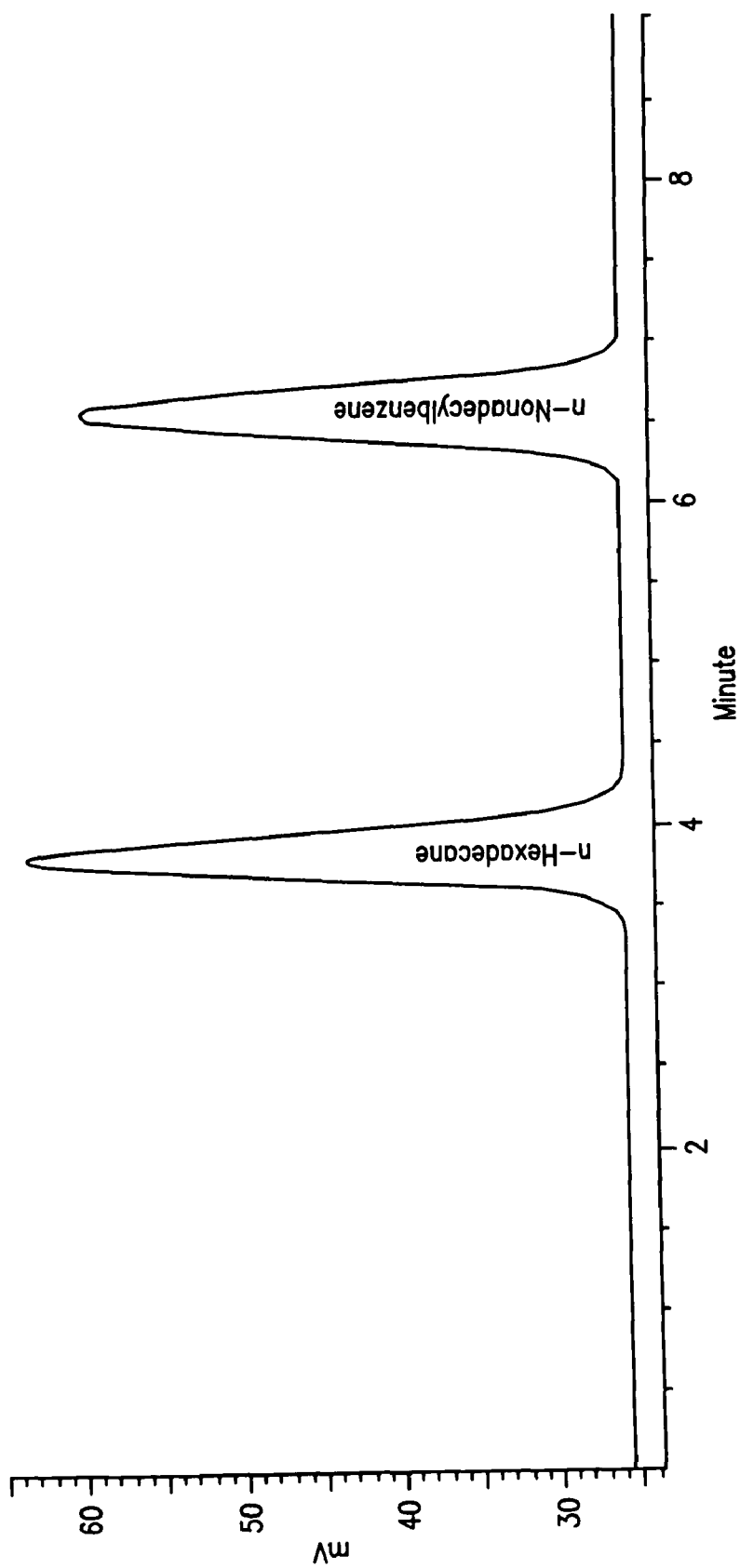
FIG. 3 shows the separation of n-Hexadecane and n-Nonadecyl-benzene 1:1 mixture using an evaporative light scattering detector (ELSD).

An illustration in FIG. 3 demonstrates that the ELSD-1000 can be used for detecting quantitatively the 550+F boiling material if the detector was optimized to operate under uncommon conditions. A mixture prepared by blending equal quantities of n-hexadecane (BP=550° F.) and n-nonadecyl-benzene (BP=650° F.) in hexane and analyzing it with the ELSD-1000. As shown in FIG. 3, the ELSD-1000 gave equal area response for 550° F. and 650° F. samples The separations were performed over $Ag^+/SCX^-$ column using 15% methylene chloride in hexane at a flow rate of 1.5 ml/min.

Chromatographic Separation

Figure 4:
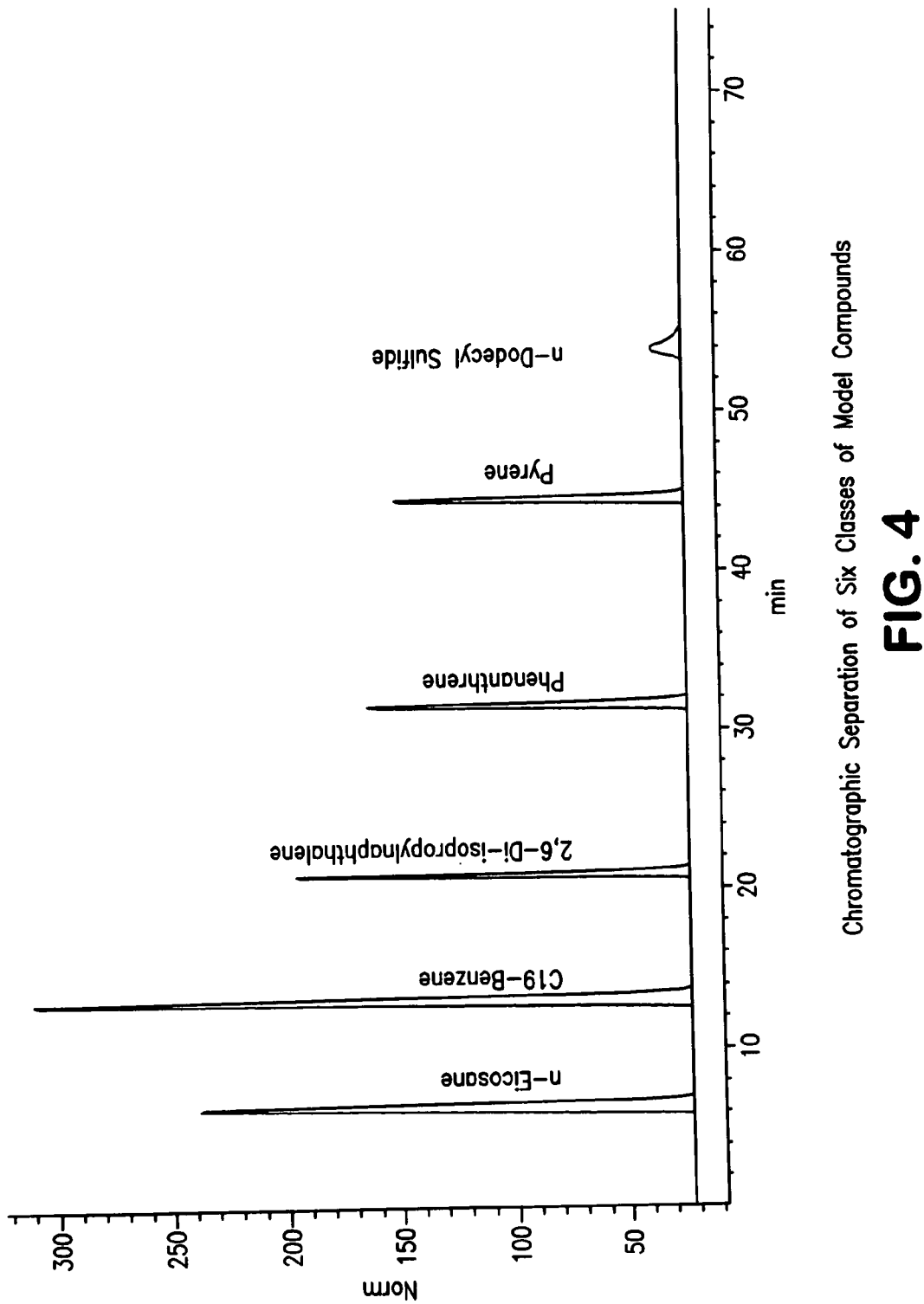
FIG. 4 shows the chromatographic separation of six classes model compounds of Example 1.
Figure 5:
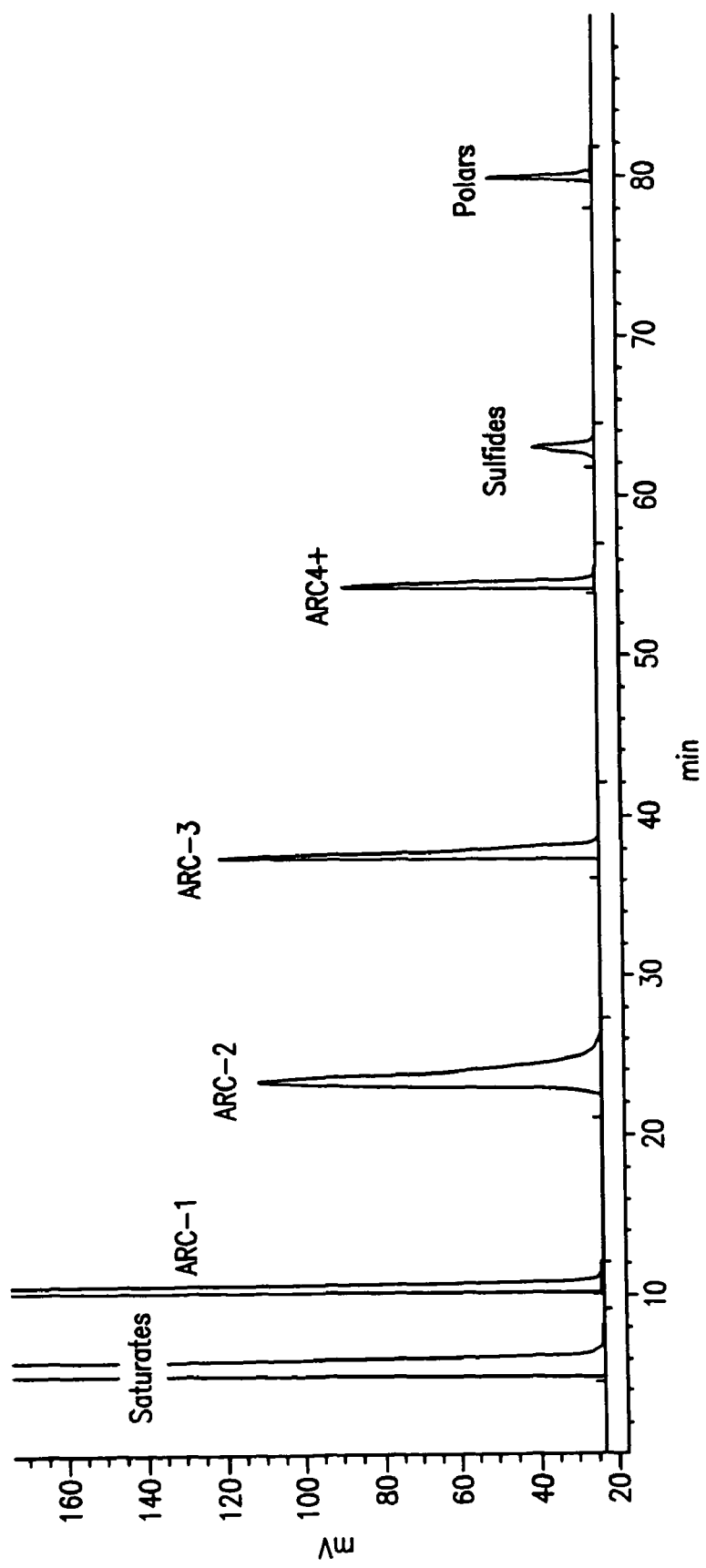
FIG. 5 shows the separation chromatogram of the petroleum distillate of Example 2.

In order to achieve separations outlined in FIGS. 4 and 5, the several model compounds and the chromatographically separated fractions of saturates (paraffinic & naphthenic), aromatics (alkyl-substituted 1-ring, 2-ring, 3-ring, and 4-ring), sulfides, and polars were chromatographed separately and in mixtures using both of the columns (DNAP & $Ag^+/SCX^-$) in series. After running many combinations of solvents (because different solvent polarity was needed for elution of different fractions) and adjusting the cut points, the solvent program provided in Table 1 along with valve switching arrangement provided in Table 4 was found to be acceptable.

TABLE 4

A summary of separation steps along with column-switching orders, valve-arrangements & their switching orders

| | | | Valve Location/VALVE #/Position/Contacts | | | |
|---|---|---|---|---|---|---|
| | | | Thermostat Valve 1 | | More Pump Valve 2 | |
| Step # | Time (min) | STEP | (Column In-line) | Position | Contact 1 | Contact 2 |
| 1 | Initial | Start-up and Transfer of "Saturates & ARC-1 + Some Sulfides" to Column 2 | Column 1 (Both Columns in-line) | Load | Closed | Open |
| 2 | 4.0 | Elution of "Saturates & (ARC-1 + Some Sulfides)" | Column 2 (Column 2 in-line) | Load | Closed | Open |
| 3 | 13.0 | Transfer of "ARC-2 + Some Sulfides" to Column 2 | Column 1 | Load | Closed | Open |
| 4 | 16.0 | Elution of "ARC-2" | Column 2 | Load | Closed | Open |
| 5 | 17.0 | Increase of ELSD Sensitivity | Column 2 | Load | Closed | Open |
| 6-9 | 23-35 | Repetition of Step # 4 & 5 for Transfer & Elution of "ARC-3 & ARC-4" | Column 1 or Column 2 | Load | Closed | Open |
| 10 | 48.0 | Elution of "Sulfides" by Backflushing Column 2 | Column 2 | Load | Closed | Open |
| 11 | 56.0 | Elution of "Polars" by Backflushing Column 1 | Column 1 (Only Column 1 in-line) | Inject | Open | Closed |
| 12 | 90.0 | System Regeneration | Column 1 | Load | Closed | Open |

| | More Pump Contacts for ELSD | | | INJECTOR | | | | | |
|---|---|---|---|---|---|---|---|---|---|
| | Signal | | | Valve 3 | | | Valve 4 | | |
| Step # | Signal | Contact 3 | Contact 4 | Position | Contact 1 | Contact 2 | Position | Contact 3 | Contact 4 |
| 1 | 1 Volt | Closed | Open | Load | Closed | Open | Load | Open | Closed |
| 2 | 1 Volt | Closed | Open | Load | Closed | Open | Load | Open | Closed |
| 3 | 1/10 Volt | Open | Closed | Load | Closed | Open | Load | Open | Closed |
| 4 | 1/10 Volt | Open | Closed | Load | Closed | Open | Load | Open | Closed |
| 5 | 1/10 Volt | Open | Closed | Load | Closed | Open | Load | Open | Closed |
| 6-9 | 1/10 Volt | Open | Closed | Load | Closed | Open | Load | Open | Closed |
| 10 | 1/10 Volt | Open | Closed | Inject | Open | Closed | Inject | Closed | Open |
| 11 | 1/10 Volt | Open | Closed | Inject | Open | Closed | Load | Open | Closed |
| 12 | 1 Volt | Closed | Open | Load | Closed | Open | Load | Open | Closed |

EXAMPLE 1

A six peak solution was prepared by dissolving approximately same amount of each of the model compounds representing the 6 classes of compounds, namely n-eicosane (saturate component), n-nonadecyl-benzene (ARC-1 component), 2,6-di-iso-propyl-naphthalene (ARC-2 component), phenanthrene (ARC-3 component), pyrene (ARC-4 component), and n-dodecyl sulfide in hexane solvent, and then analyzed using the final STAR-7 method. As shown in FIG. 4 that all the components are baseline separated. However, the peaks' shapes and hence the peak areas vary significantly from component to component. Although the peak shapes were improved by using a 2-mL stainless loop ($\frac{1}{16}$"), placed between the last switching valve and the mass detector, the peak areas remained different. The different peaks for same amounts of different components strongly suggested that each of the component peaks must be calibrated independently in order to obtain accurate quantitative analysis data.

EXAMPLE 2

A solution (100 mg in 10 ml of cyclohexane) of a petroleum distillate, which we had separated several times by preparative liquid chromatography, was also chromatographed several times using STAR7. A typical chromatogram is shown in FIG. 5.

Calibration of Mass Detector (ELSD)

Although the ELSD calibrations could be made using model compounds, we found out that the calibration curves change slightly, depending upon the type of compound chosen, for example n-eicosane (paraffinic saturate) versus cholestane (naphthenic saturate). Also, since the goal was to match the STAR7 quantitation with that of preparative HPLC separations, we decided to use a petroleum distillate (a preparative HPLC quality control sample) sample as a single calibration sample for calibration of all the START peaks over a wide range of concentrations. Because the ELSD is a non-linear detector, we had to find the best fit for the detector response against the sample amount in order to convert the peak area into the individual component amount for quantitation. After trying several combinations, we found that the square root of the peak area fits very well with the component amount over a wide range of concentrations. We also forced the fits to pass through zero intercepts.

Figure 6:
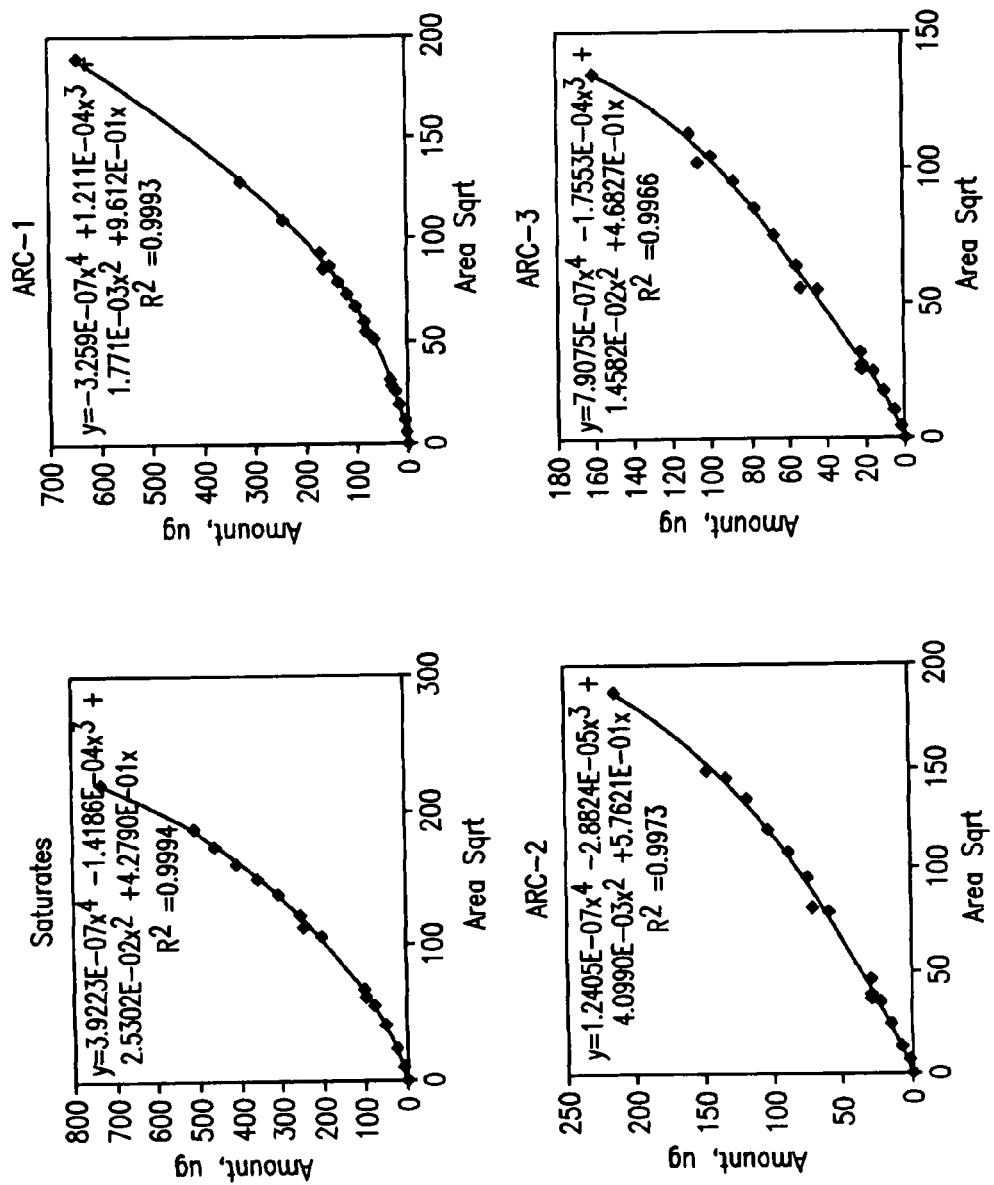
FIG. 6 shows calibration plots of saturates, aromatics, sulfides and polars of Example 2.
Figure 6:
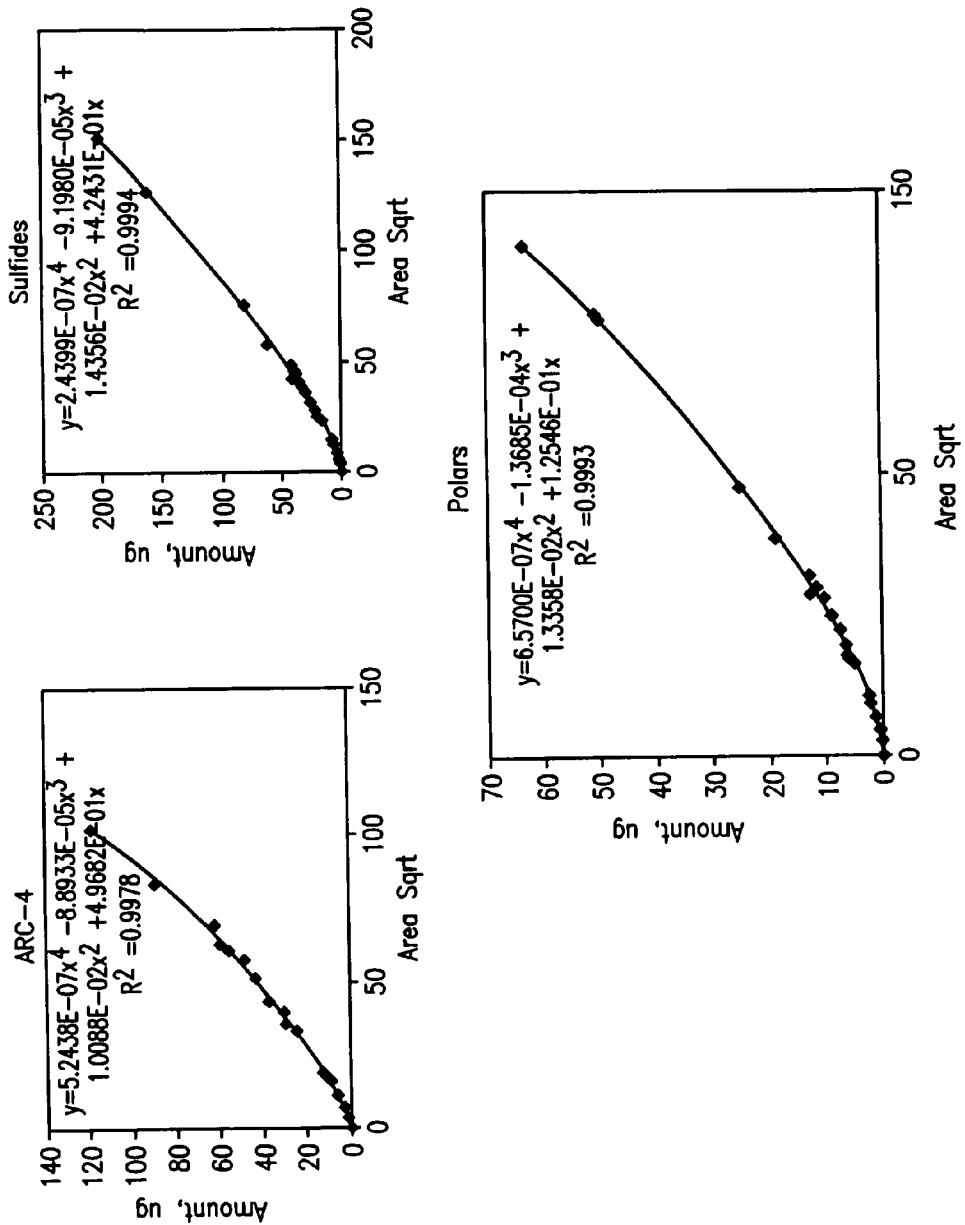

In order to obtain data for calibrations over a wide range of concentration, two solutions of the petroleum distillate were prepared by dissolving 100 milligrams and 1000 milligrams, each in 10 milliliters solution of cyclohexane. The two solutions were analyzed by making 2, 5, 10, 15, 20, 30, 40, 50, 60, 70, 80, 90, 100 microliters injections. The amount injected (micrograms) for each component was obtained using the preparative chromatographic separation data (Table 5) and then plotted against the square root of the respective peak area (FIG. 6).

TABLE 5

Preparative HPLC separation Data for a Petroleum Distillate

| Fraction | Wt % |
|---|---|
| Saturates | 48.3 ± 0.60 |
| ARC-1 | 15.9 ± 0.70 |
| ARC-2 | 14.1 ± 0.60 |
| ARC-3 | 10.6 ± 0.60 |
| ARC-4+ | 5.8 ± 0.40 |

TABLE 5-continued

Preparative HPLC separation Data for a Petroleum Distillate

| Fraction | Wt % |
|---|---|
| Sulfides | 4.0 ± 0.40 |
| Polars | 1.3 ± 0.20 |

Quantification of Seven Fractions

Once the detector has been calibrated using a petroleum distillate and the calibration plots have been generated, a sample solution (100 mg/10 ml) is analyzed. At the end of analysis, a peak area report is generated. Using the calibration fits shown in FIG. 6, the peak area of each of the seven peaks (FIG. 5) is converted into the respective amount (see below).

$$Y_{Sats} = A_{Sats}(X_{Sats})^4 + B_{Sats}(X_{Sats})^3 + C_{Sats}(X_{Sats})^2 + D_{Sats}(X_{Sats}) \quad \text{Eqn. 1}$$

$$Y_{ARC1} = A_{ARC1}(X_{ARC1})^4 + B_{ARC1}(X_{ARC1})^3 + C_{ARC1}(X_{ARC1})^2 + D_{ARC1}(X_{ARC1}) \quad \text{Eqn. 2}$$

$$Y_{ARC2} = A_{ARC2}(X_{ARC2})^4 + B_{ARC2}(X_{ARC2})^3 + C_{ARC2}(X_{ARC2})^2 + D_{ARC2}(X_{ARC2}) \quad \text{Eqn. 3}$$

$$Y_{ARC3} = A_{ARC3}(X_{ARC3})^4 + B_{ARC3}(X_{ARC3})^3 + C_{ARC3}(X_{ARC3})^2 + D_{ARC3}(X_{ARC3}) \quad \text{Eqn. 4}$$

$$Y_{ARC4} = A_{ARC4}(X_{ARC4})^4 + B_{ARC4}(X_{ARC4})^3 + C_{ARC4}(X_{ARC4})^2 + D_{ARC4}(X_{ARC4}) \quad \text{Eqn. 5}$$

$$Y_{Sulf} = A_{Sulf}(X_{Sulf})^4 + B_{Sulf}(X_{Sulf})^3 + C_{Sulf}(X_{Sulf})^2 + D_{Sulf}(X_{Sulf}) \quad \text{Eqn. 6}$$

$$Y_{Polars} = A_{Polars}(X_{Polars})^4 + B_{Polars}(X_{Polars})^3 + C_{Polars}(X_{Polars})^2 + D_{Polars}(X_{Polars}) \quad \text{Eqn. 7}$$

Where Ys, and Xs are respectively the amounts in milligrams and peak area square roots of saturates, ARC1-4, sulfides, and polars peaks. Constants As, Bs, Cs, and Ds are the fits constants (see FIG. 6).

The normalized percent mass recovery of each of the fraction is determined by multiplying the recovered amount of that fraction by 100 and then dividing it by the total amount of all fractions, e.g.

$$\text{Saturates, Wt \%} = (100 * Y_{Sats})/(Y_{Sats} + Y_{ARC1} + Y_{ARC2} + Y_{ARC3} + Y_{ARC4} + Y_{Sulf} + Y_{Polars}) \quad \text{Eqn. 8}$$

Whereas, the total mass recovery (Wt %) is determined as follows:

$$100(Y_{Sats} + Y_{ARC1} + Y_{ARC2} + Y_{ARC3} + Y_{ARC4} + Y_{Sulf} + Y_{Polars})/(\text{Amount Injected}) \quad \text{Eqn. 9}$$

Accuracy of STAR7 Data

In order to verify the accuracy of the STAR7 measurements, a variety of heavy petroleum streams were analyzed using this analytical HPLC (STAR7) and large scale preparative HPLC methods. The samples included vacuum gas oils, heavy distillates, raffinates, and extracts. We have also analyzed samples containing olefins, like coker products.

Figure 7:
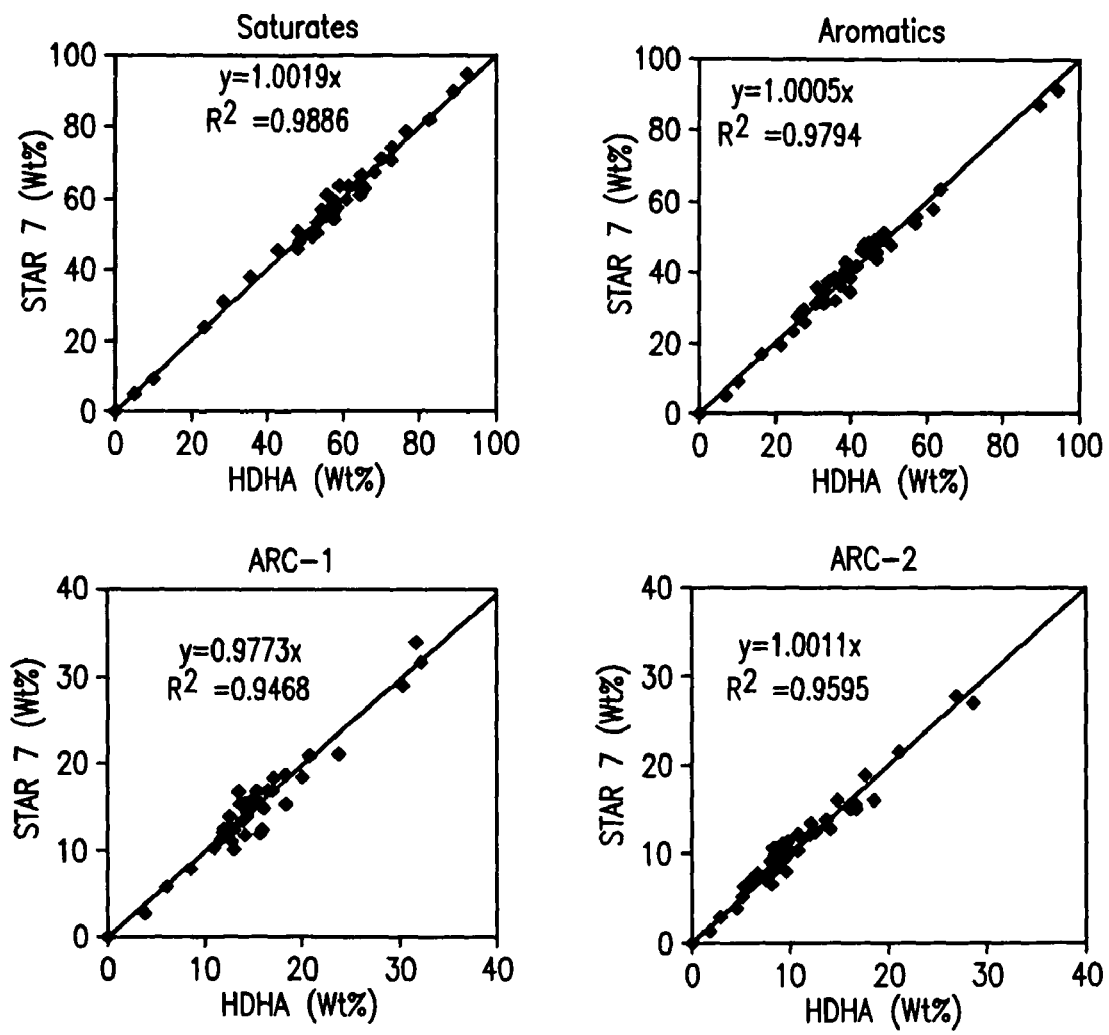
FIG. 7 shows comparisons for measurements using the present invention and the preparative HPLC separations.
Figure 7:
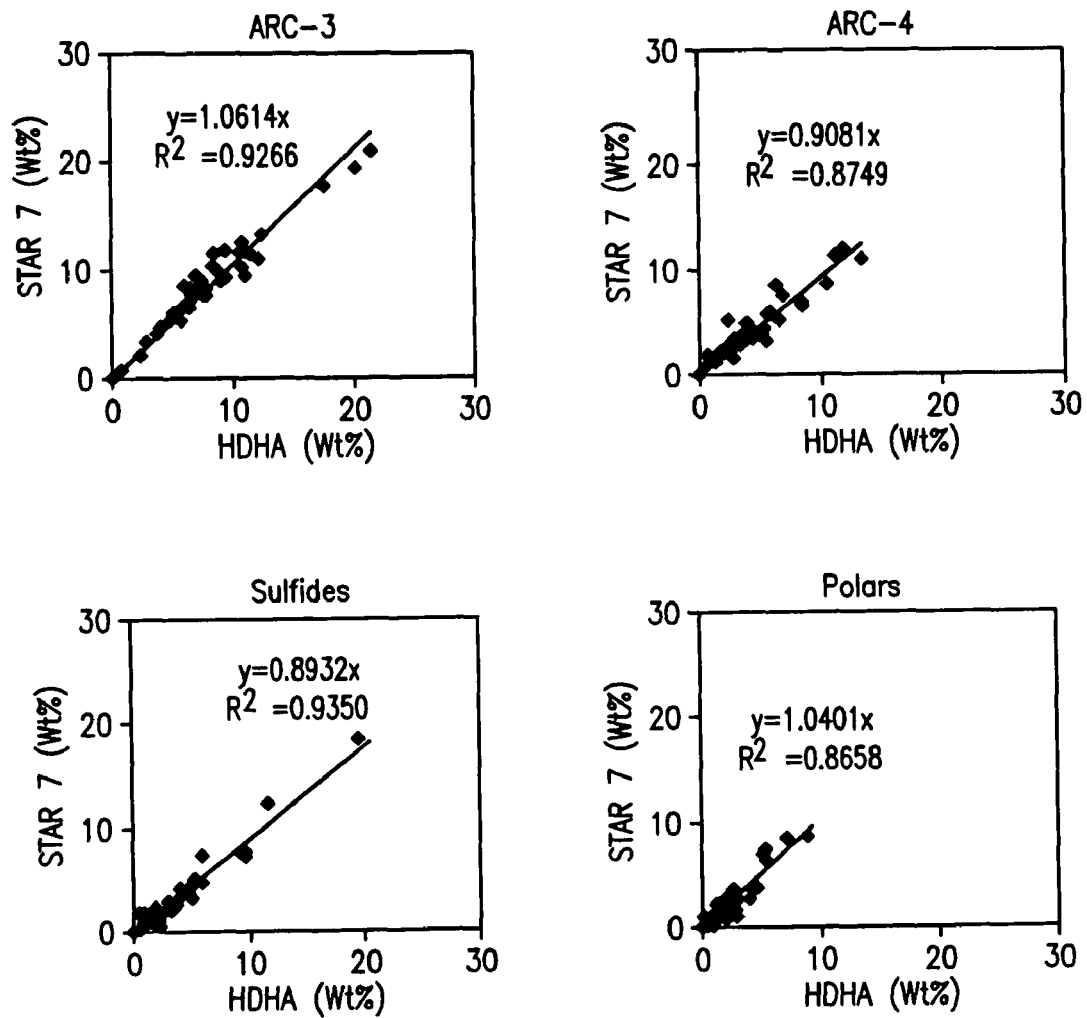

With the exception of extracts and Coker samples, we found that the comparison between the preparative and the analytical HPLC method (STAR7) results (see FIG. 7 and Table 6) were very good for all of the 7 fractions The STAR7 results can be used along with other analyses such as density, GC-simulated distillation, % S and % N as targets for "synthesis" of relatively accurate full compositional information from the gas oil 'models of compostion'.

EXAMPLE 3

Figure 9:
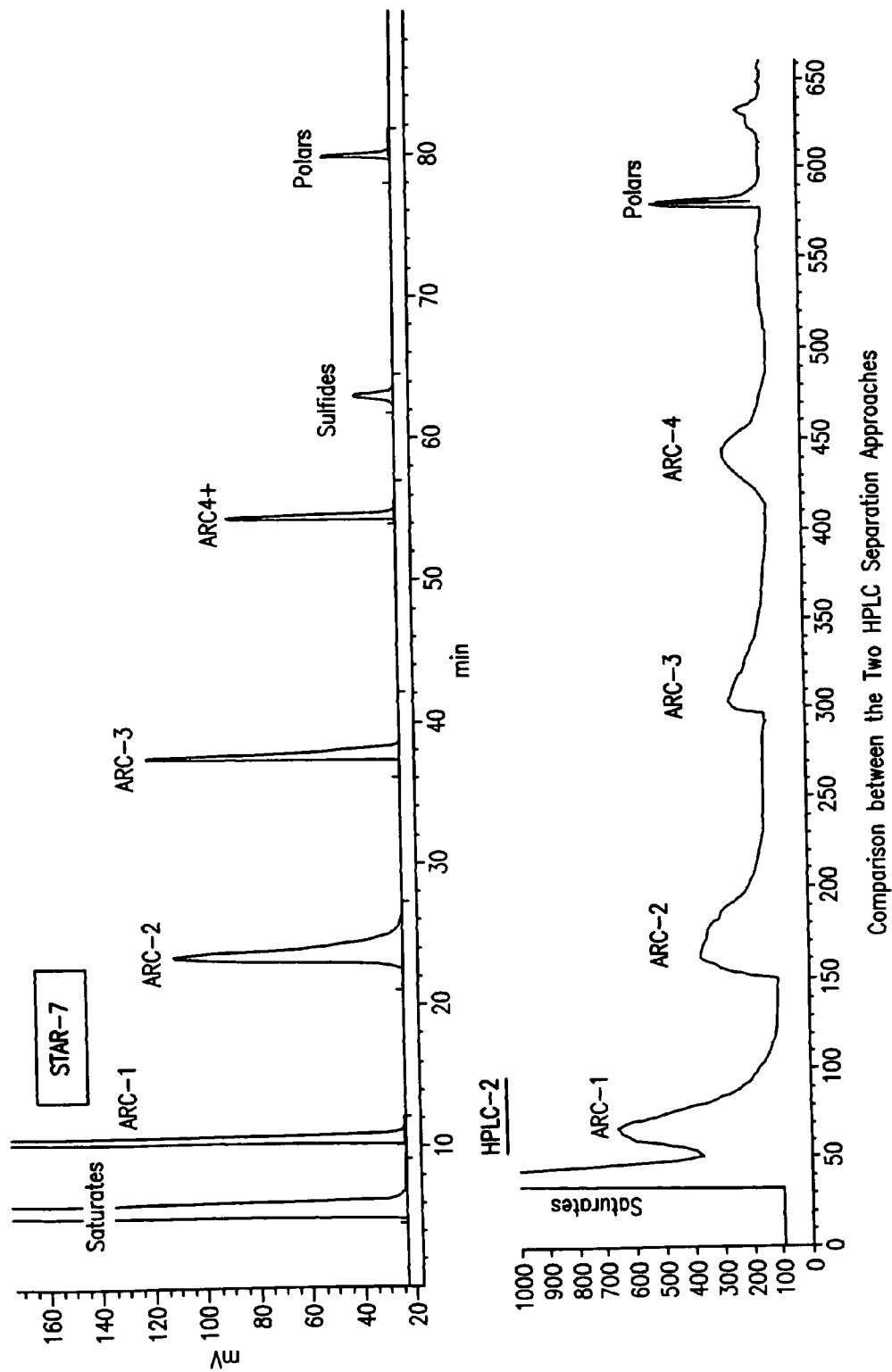
FIG. 9 shows comparison between HPLC-2 and STAR7 separation methods.

For comparison purposes, a solution (Approx. 100 mg in 10 ml of cyclohexane) of a petroleum distillate was analyzed using the two analytical (STAR7 and HPLC-2) methods. The two chromatograms shown in FIG. 9 clearly demonstrate the superiority of the STAR7 method. In STAR7 in addition to the saturates and ARC-1 baseline separation, the rest of the 5 components are also well-defined and baseline separated. Also, STAR7 provides quantition of an additional fraction, the sulfides.

desired ratio for the specific duration at a selected rate of up to 40 ml/min. The refractive index detector, Shodex RI-72, purchased from J. M. Science Inc. (New York) was used to observe the goodness of the separation between saturates and aromatics. Four switching valves (three 6-port and one 4-port) are used in order to have the options of back-flushing both of the 'sulfides' and 'polars' columns independently.

TABLE 6

Comparison between Analytical HPLC (STAR7) and Preparative HPLC Separations Data

| Sample | Saturates Prep-HPLC | STAR 7 | ARC-1 Prep-HPLC | STAR 7 | ARC-2 Prep-HPLC | STAR 7 | ARC-3 Prep-HPLC | STAR 7 | ARC-4 Prep-HPLC | STAR 7 | Sulfides Prep-HPLC | STAR 7 | Polars Prep-HPLC | STAR 7 |
|---|---|---|---|---|---|---|---|---|---|---|---|---|---|---|
| QC-1 | 48.3 | 50.7 | 16.0 | 14.8 | 14.1 | 12.8 | 10.6 | 10.2 | 5.9 | 5.8 | 4.0 | 4.2 | 1.3 | 1.4 |
| QC-2 | 23.8 | 23.8 | 14.7 | 15.7 | 17.7 | 18.8 | 17.6 | 17.8 | 13.3 | 10.7 | 5.8 | 4.7 | 7.2 | 8.5 |
| Blend-1* | 5.5 | 5.0 | 32.2 | 31.6 | 28.5 | 26.9 | 21.4 | 20.9 | 11.8 | 11.7 | 0.5 | 1.8 | 0.1 | 1.0 |
| Blend-2* | 10.2 | 9.2 | 30.5 | 28.9 | 26.9 | 27.6 | 20.2 | 19.4 | 11.2 | 11.0 | 0.8 | 1.9 | 0.3 | 1.1 |
| Blend-3* | 72.7 | 73.9 | 8.4 | 7.8 | 7.4 | 7.1 | 5.6 | 5.3 | 3.1 | 3.0 | 2.1 | 2.2 | 0.7 | 0.7 |
| Blend-4* | 89.1 | 89.7 | 3.4 | 2.9 | 3.0 | 2.8 | 2.2 | 2.1 | 1.2 | 1.2 | 0.8 | 0.9 | 0.3 | 0.2 |
| Sample-1 | 23.8 | 23.8 | 14.7 | 15.7 | 17.7 | 18.8 | 17.6 | 17.8 | 13.3 | 10.7 | 5.8 | 4.7 | 7.2 | 8.5 |
| Sample-2 | 53.4 | 50.3 | 17.0 | 17.0 | 14.8 | 16.0 | 9.2 | 11.8 | 3.3 | 3.4 | 0.7 | 0.5 | 1.6 | 1.0 |
| Sample-3 | 64.6 | 64.3 | 11.7 | 11.3 | 8.3 | 8.3 | 6.4 | 7.7 | 4.1 | 3.6 | 3.4 | 2.7 | 1.5 | 1.8 |
| Sample-4 | 28.1 | 31.2 | 23.7 | 21.0 | 18.6 | 16.0 | 12.3 | 13.3 | 6.8 | 7.4 | 5.9 | 7.4 | 4.6 | 3.8 |
| Sample-5 | 48.7 | 47.8 | 31.7 | 33.9 | 9.3 | 10.0 | 4.7 | 5.4 | 2.8 | 1.5 | 0.8 | 0.6 | 2.0 | 0.8 |
| Sample-6 | 0.0 | 0.0 | 0.0 | 0.0 | 0.0 | 0.0 | 0.0 | 0.0 | 0.0 | 0.0 | 0.0 | 0.0 | 0.0 | 0.0 |
| Sample-7 | 28.7 | 31.7 | 20.8 | 20.6 | 16.6 | 14.9 | 10.6 | 11.8 | 8.4 | 6.4 | 9.6 | 7.2 | 5.3 | 7.4 |
| Sample-8 | 63.6 | 63.7 | 14.4 | 14.1 | 8.7 | 8.7 | 6.3 | 6.6 | 2.2 | 2.6 | 2.7 | 2.1 | 2.1 | 2.2 |
| Sample-9 | 92.1 | 94.7 | 3.8 | 2.6 | 1.9 | 1.2 | 0.7 | 0.7 | 0.4 | 0.8 | 0.2 | 0.0 | 1.0 | 0.0 |
| Sample-10 | 59.2 | 63.4 | 18.3 | 15.2 | 9.7 | 7.8 | 6.1 | 6.9 | 1.5 | 1.8 | 3.7 | 2.6 | 1.5 | 2.2 |
| Sample-11 | 61.2 | 59.3 | 15.1 | 15.7 | 10.0 | 10.1 | 7.2 | 9.0 | 3.3 | 3.5 | 2.2 | 1.5 | 1.1 | 0.9 |
| Sample-12 | 65.9 | 62.8 | 12.7 | 12.6 | 9.8 | 11.3 | 5.9 | 8.5 | 2.7 | 2.5 | 1.2 | 0.8 | 1.8 | 1.4 |
| Sample-13 | 42.9 | 45.6 | 12.5 | 13.8 | 16.2 | 15.0 | 11.3 | 11.5 | 6.5 | 5.0 | 9.0 | 7.7 | 1.6 | 1.4 |
| Sample-14 | 57.7 | 59.3 | 13.8 | 13.3 | 9.6 | 10.0 | 7.7 | 8.3 | 5.3 | 4.3 | 3.9 | 3.3 | 1.9 | 1.4 |
| Sample-15 | 48.6 | 46.1 | 13.5 | 15.2 | 9.1 | 11.0 | 10.5 | 11.6 | 10.4 | 8.4 | 5.4 | 4.7 | 2.5 | 3.0 |
| Sample-16 | 58.8 | 57.6 | 13.5 | 16.7 | 8.5 | 9.8 | 6.4 | 7.9 | 5.4 | 3.0 | 4.6 | 3.7 | 2.8 | 1.1 |
| Sample-17 | 65.0 | 66.5 | 14.2 | 11.8 | 8.2 | 6.5 | 7.6 | 7.7 | 2.4 | 5.0 | 1.9 | 2.0 | 0.7 | 0.4 |
| Sample-18 | 70.1 | 71.1 | 15.9 | 12.3 | 5.4 | 6.2 | 3.9 | 4.8 | 2.0 | 2.5 | 1.9 | 2.3 | 0.8 | 0.8 |
| Sample-19 | 76.5 | 78.5 | 12.9 | 10.2 | 4.6 | 3.8 | 2.8 | 3.3 | 0.8 | 1.8 | 2.0 | 1.9 | 0.5 | 0.5 |
| Sample-20 | 56.2 | 57.1 | 15.6 | 12.0 | 8.1 | 9.0 | 9.3 | 9.4 | 6.3 | 8.2 | 3.0 | 2.9 | 1.5 | 1.5 |
| Sample-21 | 48.8 | 48.4 | 20.1 | 18.4 | 13.7 | 13.8 | 8.4 | 11.5 | 3.8 | 4.7 | 2.2 | 0.5 | 3.0 | 2.7 |
| Sample-22 | 57.8 | 54.2 | 15.3 | 16.7 | 12.0 | 12.2 | 6.8 | 9.5 | 4.2 | 3.9 | 1.6 | 0.8 | 2.1 | 2.8 |
| Sample-23 | 35.8 | 38.0 | 12.6 | 11.1 | 21.2 | 21.4 | 12.1 | 11.0 | 4.3 | 3.8 | 11.6 | 12.3 | 2.4 | 2.3 |
| Sample-24 | 55.6 | 60.9 | 14.0 | 11.8 | 8.3 | 7.8 | 10.9 | 9.5 | 6.1 | 5.3 | 3.1 | 2.0 | 1.9 | 2.7 |
| Sample-25 | 51.4 | 50.9 | 16.3 | 16.7 | 12.5 | 12.3 | 8.7 | 9.0 | 3.8 | 3.5 | 5.3 | 5.0 | 1.9 | 2.6 |
| Sample-26 | 61.6 | 60.6 | 12.9 | 12.5 | 8.4 | 9.4 | 6.9 | 8.2 | 4.3 | 4.1 | 1.8 | 1.2 | 4.1 | 4.0 |
| Sample-27 | 54.4 | 56.7 | 14.9 | 15.3 | 10.7 | 10.3 | 7.7 | 7.7 | 3.4 | 2.8 | 5.0 | 4.3 | 4.0 | 2.8 |
| Sample-28 | 57.4 | 55.3 | 16.5 | 17.0 | 9.2 | 11.1 | 8.8 | 8.9 | 3.8 | 3.5 | 1.7 | 0.7 | 2.6 | 3.6 |
| Sample-29 | 64.5 | 61.1 | 11.8 | 11.9 | 8.3 | 10.6 | 6.4 | 8.4 | 4.1 | 4.3 | 3.4 | 2.2 | 1.5 | 1.6 |
| Sample-30 | 53.2 | 53.2 | 14.1 | 15.4 | 11.0 | 12.1 | 8.8 | 9.6 | 5.1 | 3.6 | 4.8 | 4.5 | 2.9 | 1.6 |
| Sample-31 | 48.0 | 45.9 | 16.9 | 18.2 | 12.2 | 13.3 | 8.3 | 10.4 | 5.6 | 5.7 | 4.9 | 3.2 | 4.2 | 3.4 |
| Sample-32 | 52.0 | 49.1 | 18.3 | 18.5 | 12.0 | 13.4 | 8.6 | 10.1 | 3.9 | 4.2 | 2.8 | 2.2 | 2.3 | 2.5 |
| Sample-33 | 28.7 | 30.4 | 20.7 | 20.9 | 16.6 | 15.4 | 10.6 | 12.5 | 8.4 | 6.8 | 9.6 | 7.6 | 5.3 | 6.3 |
| Sample-34 | 55.8 | 55.4 | 14.8 | 14.8 | 11.0 | 11.9 | 7.4 | 7.6 | 3.7 | 3.2 | 6.0 | 4.8 | 1.3 | 2.2 |
| Sample-35 | 72.6 | 70.6 | 10.9 | 10.3 | 6.3 | 7.0 | 5.6 | 6.4 | 2.9 | 3.4 | 1.2 | 1.1 | 0.5 | 0.9 |
| Sample-36 | 82.7 | 82.4 | 6.1 | 5.8 | 5.2 | 5.1 | 3.6 | 4.1 | 1.3 | 1.5 | 0.4 | 0.2 | 0.8 | 0.8 |
| Sample-37 | 68.1 | 67.7 | 11.9 | 12.3 | 6.7 | 7.6 | 5.0 | 6.1 | 3.8 | 3.3 | 2.2 | 1.1 | 2.3 | 2.0 |
| Sample-38 | 63.8 | 63.7 | 14.2 | 13.6 | 9.4 | 9.5 | 6.5 | 7.1 | 3.0 | 3.1 | 2.3 | 1.8 | 0.9 | 1.2 |

*Blends 1-4 are prepared by mixing the appropriate amounts of the pure 'total saturates' and 'total aromatics' fractions obtained from the preparative HPLC separations.

Preparative HPLC Separations

Two large scale preparative HPLC separation techniques were used. These techniques are outlined in FIG. 8 as 'Step I' and 'Step II' and are discussed below:

Preparative HPLC Step I Separation Details

In the preparative chromatographic separation Step I (Silica Gel Separation), about 5 grams of the sample is fractionated into four classes of compounds: 'saturates', 'aromatics', 'sulfides', and 'polars'. (see FIG. 8).

The HPLC system is equipped with a Waters quaternary solvent delivery pump and a dual wavelength UV detector. The solvent delivery pump can be programmed to deliver either one of the four different solvents or a mixture in a desired ratio for the specific duration at a selected rate of up to 40 ml/min. The refractive index detector, Shodex RI-72, purchased from J. M. Science Inc. (New York) was used to observe the goodness of the separation between saturates and aromatics. Four switching valves (three 6-port and one 4-port) are used in order to have the options of back-flushing both of the 'sulfides' and 'polars' columns independently. One 6-port switching valve was converted to be used as an injector. One large volume injection loop was installed to accommodate up to 40 ml of the sample solution in cyclohexane. A fraction-collector was used to collect all of the necessary fractions generated in a separation.

The main column (1000×30 mm) and the polars column (500×21 mm) are laboratory packed with approximately 650 g and 120 g of freshly activated silica gel (grade 923, 100-200 mesh, 60A°), respectively. The main column is found to stay useable for a year or more based upon the number of separations performed. The polars column not only adsorbs polars but also acts as a guard column and is, therefore, replaced each time a separation is performed.

A commercially prepared silver-loaded silica gel-based-sulfonic acid (Ag$^+$/SCX$^-$-silica gel-Strong Cation Exchange) column (250×21 mm) is used to isolate sulfides. The Ag$^+$/SCX$^-$-silica gel column (250×21 mm) is purchased from Phenomenex.

An instrument method controlled by the Waters Millennium$^{R32}$ chromatographic management system, which controls all the switching valves and the fraction collection valve, was created in such a way that the main column is regenerated at the end of the separation run.

At the system start up, the solvent delivery system is programmed to run cyclohexane at a flow rate of 20 ml/min through all the three columns. After about 30-60 min, once the system is stabilized, a 40 ml cyclohexane solution of ~5 g sample is injected. Initially, the total effluent after passing through the three columns is passed through the UV and RI detectors and then to the fraction collector. This arrangement allows saturates to be separated and eluted. During this step after the saturates are eluted, the pump is switched to run toluene (100%) which will allow aromatics to be eluted out and the polars and sulfides to be retained by the polars and sulfides column, respectively. The polars and sulfides are back-flushed individually. Sulfides are back-flushed using 500 ml of each of the 4% and 20% methanol in toluene, whereas polars are recovered using 1000 ml of 100% methanol.

In addition to collecting saturates, aromatics, sulfides and polars fractions, six (each about 80-120 ml, except beaker-1 which contains 250 ml) in-between saturates and aromatics fractions are collected in beakers to establish an acceptable cut-point between saturates and aromatics depending upon the fraction weights (mg) in the beakers after solvent evaporation. Final mass recoveries of all four fractions were determined by fraction weights after solvent evaporation.

Preparative HPLC Step II Separation Details

Figure 8:
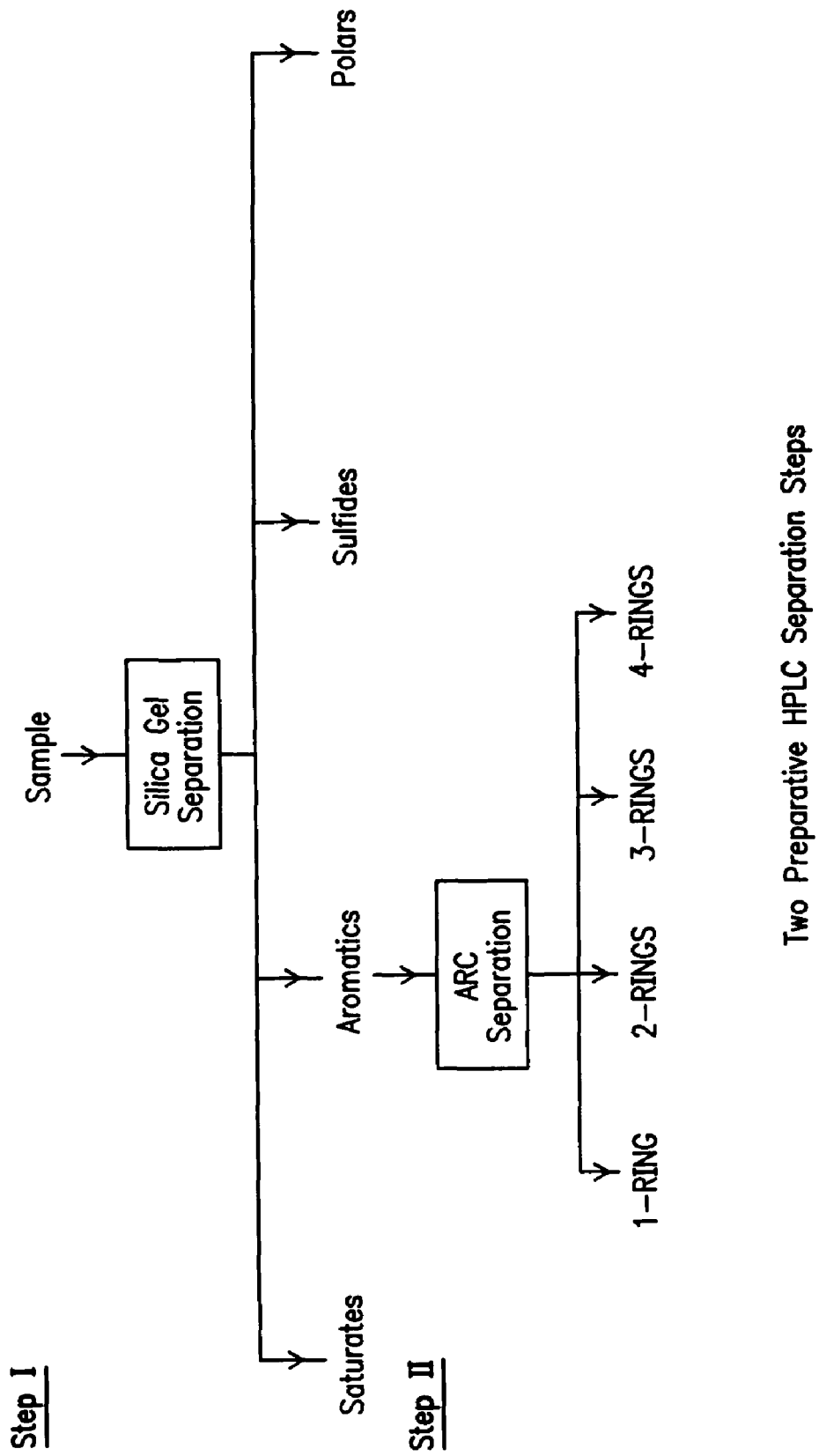
FIG. 8 shows a schematic diagram of the two preparative HPLC separations steps.

A portion of the aromatics is further fractionated using a low temperature (−40° C.) Aromatic Ring Class (ARC) preparative HPLC separation Step II (FIG. 8). The sub-ambient (−40° C.) ARC system can handle only about 200 mg of aromatics.

The ARC HPLC system consisted of a Waters quaternary solvent delivery systems (W600), a manual 2 ml sample loop injector, a 10-position electrically actuated valve (Valco Model ECSD10P), a Valco backflush valve (EC6V), and a Waters photodiode-array detector (Model PDA-991). A column (50 cm×25 mm I.D.) pre-packed with 10 micron particles of [3-(2,4-dinitroanilino-)-propyl]-silica (DNAP-silica or DNAP) was supplied by ES Industries (Marlton, N.J.). The column always remains completely immersed in a continuous flow of methanol maintained at −40±1° C. with a constant temperature refrigerated re-circulating bath (Neslab Model LT-50DD). The commercially available HPLC grade mobile phases, n-pentane and methylene chloride, were used after overnight drying over freshly activated 4A molecular sieves (8-12 mesh, purchased from Aldrich Chemical Company) at 180° C. under vacuum for about 24 hrs.

In a typical run, the initial mobile phase (100% n-pentane) was passed through the HPLC system for about 60 min at a flow rate of 8.0 ml/min in order to ensure that the sample loop, the column, the detector cell and the valves are thoroughly cleaned and equilibrated with n-pentane. The photodiode-array detector (PDA-991) was set to measure the spectra in the range of 190-400 nm at intervals of 1.3 nm every 25 sec over a period of 600 min. A 1-mm path length cell was used for the UV/V is measurements.

The aromatics were eluted under increasing aromatic ring classes (ARC) of compound, namely ARC-1, ARC-2, ARC-3 and ARC4+ depending upon the times for which they were retained in the column. Specifically, a molecule was classified as ARC-1 (e.g., toluene with 1 aromatic ring) if its retention time was less than 120 min, ARC-2 (e.g. naphthalene) if it was between 120 min and 330 min and ARC-3 (e.g. phenanthrene) if it was between 330 min and 480 min. The chromatographic column was back flushed beyond 480 min; consequently any molecule whose retention time was greater than 480 min was lumped into ARC-4+. The chromatographic retention time data (in minutes) for the different pure molecules investigated are summarized elsewhere (Ghosh et al., Energy & Fuels, vol 20, No. 2, pp 609-619 (2006).

The four aromatic fractions were eluted using either the pure solvents or their mixtures of different solvent polarity. Details are given in Table 7.

TABLE 7

Eluting solvent composition for eluting ARC fractions

| ARC Fraction | Eluting Solvent |
|---|---|
| ARC-1 | 100% Pentane |
| ARC-2 | 4% Methylene Chloride in Pentane |
| ARC-3 | 20% Methylene Chloride in Pentane |
| ARC-4 | 100% Methylene Chloride |

Final mass recoveries of all four fractions were determined by fraction weights after solvent evaporation.

What is claimed is:

1. A method for the chromatographic analysis of hydrocarbon oil comprising:
   Step 1: passing a mixture of the hydrocarbon oil and a first solvent sequentially through a 2,4-dinitro-anilinopropyl-silica gel (DNAP) and a silver ion strong cation ion exchange column (Ag$^+$/SCX$^-$) to elute pure 'saturate' fraction of said oil and sending it to an evaporative light scattering detector (ELSD),
   Step 2: passing a solvent through Ag$^+$/SCX$^-$ to elute a fraction of said hydrocarbon oil, repeating steps 1 and 2 only with solvents chosen to elute different fractions of said hydrocarbon oil, back-flushing DNAP and Ag$^+$/SCX$^-$ to elute different fractions, sending said eluting fractions to an evaporative light scattering detector (ELSD),
   Step 3: detecting light scattered by said eluting fractions; and
   Step 4: determining the composition of said hydrocarbon oil from said detected scattered light.

2. The method of claim 1 wherein said fractions include at least one of saturates, aromatic ring classes (1-14), sulfides and polars.

3. The method of claim 1 wherein said solvents include hexane, methylene chloride and toluene in various proportions, methylene chloride, toluene and iso-propanol in various proportions.

4. The method of claim 1 wherein said ELSD has a lower temperature of 550° F.

5. The method of claim 1 wherein said fraction includes saturates.

6. The method of claim 1 wherein said fraction includes aromatic ring classes.

7. The method of claim 1 wherein said fraction includes sulfides.

8. The method of claim 1 wherein said fraction includes polars.

9. A system for chromatographic analysis of hydrocarbon oil comprising a solvent delivery system for supplying at least one of a plurality of solvents or mixtures thereof for use in connection with the chromatographic analysis of the hydrocarbon oil, an auto-sampler, wherein the solvent delivery system being operatively connected to the auto-sampler, a set of switching valves, wherein the auto-sampler being operatively connected to at least one switching valve of the set of switching valves, a 2,4-dinitro-anilinopropyl-silica gel (DNAP) exchange column, wherein the DNAP exchange column being operatively connected to at least one switching valve of the set of switching valves a silver ion strong cation ion exchange column ($Ag^+$/$SCX^-$), wherein the cation ion exchange column being operatively connected to at least one switching valve of the set of switching valves, and an evaporative light scattering detector (ELSD), wherein the ELSD being operatively connected to at least one switching valve of the set of switching valves.

* * * * *